United States Patent [19]

Müller

[11] 3,931,278

[45] Jan. 6, 1976

[54] PROCESS FOR PREPARING 5-OXOHEXANE-NITRILE

[75] Inventor: Werner Müller, Kelkheim, Taunus, Germany

[73] Assignee: Hoechst Aktiengesellschaft, Frankfurt am Main, Germany

[22] Filed: June 11, 1974

[21] Appl. No.: 478,263

[30] Foreign Application Priority Data

June 13, 1973 Germany............................ 2329923

[52] U.S. Cl. ............................................. 260/465.1
[51] Int. Cl.$^2$................ C07C 120/00; C07C 121/34
[58] Field of Search ................................. 260/465.1

[56] References Cited
UNITED STATES PATENTS

| | | | |
|---|---|---|---|
| 2,768,962 | 10/1956 | Krimm ......................... | 260/465.5 X |
| 2,850,519 | 9/1958 | Krimm ......................... | 260/465.1 X |
| 3,686,262 | 8/1972 | Groen et al. .................... | 260/465.1 |
| 3,708,515 | 1/1973 | Thoma et al. .................. | 260/465.1 X |
| 3,780,082 | 12/1973 | Deumens et al. ................ | 260/465.1 |
| 3,780,083 | 12/1973 | Deumens et al. ................ | 260/465.1 |
| 3,816,503 | 6/1974 | Poelvoorde et al. ............. | 260/465.1 |
| 3,821,274 | 6/1974 | Beekhuis et al. ............... | 260/465.5 X |
| 3,855,266 | 12/1974 | Beekhuis ........................ | 260/465.1 |

*Primary Examiner*—Joseph P. Brust
*Attorney, Agent, or Firm*—Curtis, Morris & Safford

[57] ABSTRACT

Process for preparing 5-oxohexane-nitrile by reaction of acetone with acrylonitrile at elevated temperatures in the presence of an acid and a compound selected from the group consisting of primary amines, aliphatic amino alcohols, aliphatic amino carboxylic acids with primary amino groups or Schiff bases and in the presence of a minor quantity of water.

5 Claims, No Drawings

PROCESS FOR PREPARING 5-OXOHEXANE-NITRILE

A possibility for preparing 5-oxohexane-nitrile well known to those skilled in the art is the addition of acrylonitrile to acetone, if the reaction is carried out in the presence of a small quantity of acid and of a primary amine or of a compound being able to form a primary amine.

5-oxohexane-nitrile is an important intermediary product for other compounds, for example $\alpha$-picoline or resorcinol.

A drawback of this known process is its poor yield in 5-oxohexane-nitrile, calculated on the acetone spent and on primary amine, mainly due to self-condensation of the acetone while forming diacetone-alcohol, mesityl-oxide and products of higher molecular weights which cannot be distilled.

Therefore, subject of the present invention is to prevent the formation of these undesirable by-products in course of the above-mentioned process. Further object is to prevent the double addition of acrylonitrile to acetone and to improve the yield in 5-oxohexane-nitrile, calculated on the consumption of catalyst.

Now, a process has been found for the preparation of 5-oxohexane-nitrile by reaction of acetone with acrylonitrile at elevated temperatures in the presence of an acid and of primary amines, aliphatic amino-alcohols, aliphatic amino-carboxylic acids with a primary amino group or Schiff bases, wherein the reaction is carried out in the presence of 0.2 to 5 weight percent of water, calculated on the reaction mixture.

In the past it was understood in the art that the presence of water in the reaction mixture would be undesirable upon cyanoethylation of ketones, for three reasons:

1. The ketimines formed from a ketone and a primary amine are considered to be reactive intermediates upon the ketone-cyano-ethylation. German Offenlegungsschrift No. 2020143 describes the cyanoethylation of pure ketimines, recommending particularly to keep the presence of water in the reaction mixture as low as possible, because acetone imines easily decompose with water.
2. It has been described (Chemical Abstracts 74, 12 49 44 h (1971)) that water prevents the cyano-ethylation of ketones in the presence of a catalyst consisting of a primary amine and a carboxylic acid.
3. It was to be expected that under the basic reaction conditions water reacts with acryonitrile to yield hydroxypropionitrile and bis-cyano-ethylether thus causing a loss in acrylonitrile.

Therefore, it is very surprising that the addition of a limited quantity of water to the reaction mixture considerably increases the yield in 5-oxohexane-nitrile.

In the process of the invention the following acids may be used — for example —: carboxylic acids such as formic acid, acetic acid, butyric acid, benzoic acid, adipic acid or mineral acids such as hydrochloric acid or phosphoric acid. The acid is added at the rate of — generally — from 0.001 to 0.02 mole, preferably from 0.002 to 0.01 mole, per mole of acrylonitrile.

Among the primary amines, aliphatic amino alcohols, aliphatic amino-carboxylic acids and Schiff bases acting as catalysts, the following are cited as examples: methylamine, ethylamine, n-propylamine, isopropylamine, n-butylamine, amylamine, cyclohexylamine, benzylamine, aniline, $\epsilon$-aminocapronic acid, aminoethanol, and Schiff bases derived from acetone and the above-mentioned primary amines. The quantity of the primary amine can vary within wide limits, generally amounting to from 0.01 to 0.2 mole per mole of acrylonitrile.

Advantageously, the catalysts should be chosen from among those which have boiling points below that of 5-oxohexanenitrile, so that they can be re-used after work-up by distillation.

The reaction mixture contains water at the rate of from 0.2 to 5 weight percent, preferably from 1 to 3 wt.%. To some extent, the optimum water concentration depends on the quantity of amine added.

Usually, the molar proportion of acetone to be reacted to acrylonitrile is 1 : 1 to 20 : 1, preferably 3 : 1 to 8 : 1.

Preferably, the acrylonitrile-conversion rate is not superior to 90 %, since otherwise secondary reactions occur - due to prolonged reaction time and higher reaction temperatures which are necessary for a conversion rate of more than 90 %.

The most favorable reaction temperature depends on the nature and quantity of the catalyst used and on the portion of water contained in the reaction mixture. As a rule, the operating range is from 50° to 250°C, preferably from 130° to 200°C. The pressure is not of critical importance, though — in general — operations are carried out at pressures from normal to 50 atm., preferably at the vapour pressure corresponding to the reaction temperature.

The reaction can be performed as well with a solvent or without. So as to prevent a polymerization of the acrylonitrile in course of the reaction, the addition of a small quantity of a polymerization-inhibitor such as hydroquinone is in general advantageous.

The following examples illustrate the invention.

EXAMPLES 1 – 11

A mixture of acetone, acrylonitrile, benzoic acid, isopropylamine, water and hydroquinone is heated to a certain temperature (cf. Table) for 1 hour in a 5 liter - autoclave. The reaction mixture, consisting of acetone, acrylonitrile, isopropylamine, mesityloxide, diacetone alcohol, N-cyanoethylisopropylamine, 5-oxohexane-nitrile, $\gamma$-acetyl-pimelic acid nitrile and a minor quantity of material which cannot be distilled, is submitted to analysis by gas chromatography. The larger part of the non-reacted acetone, acrylonitrile and isopropylamine is evacuated in a rotation evaporator. Same can be re-used for a new batch or, in case of a continuously operated reaction, fed back directly into the reactor.

The residue in the rotation evaporator is submitted to vacuum-distillation. The first fraction up to a boiling point of 30°C (170 mm) contains the remaining acetone and acrylonitrile. The second fraction up to a boiling point of 72°C (130 mm) includes mesityloxide, diacetone alcohol and water passing over as ternary azeotrope. The third fraction having a boiling point of 86°C (12 mm) contains N-cyanoethyl-isopropylamine. This latter can be submitted to thermal decomposition to yield acrylonitrile and isopropylamine and, therefore, does not mean a loss in acrylonitrile or isopropylamine. The next fraction at a boiling point of 106°C (12 mm) consists of pure 5-oxohexane-nitrile. The final fraction up to a boiling point of 150° – 160°C (6 mm) consists essentially of $\gamma$-acetylpimelic acid nitrile.

The examples show the improvement in the yield of 5-oxohexane-nitrile (OHN) in respect to acrylonitrile (AN), acetone (ACT) and isopropylamine (IPA) by addition of different quantities of water to the reaction mixture at different concentrations of acrylonitrile and isopropylamine.

reaction conditions:
quantity applied: acetone: 2320 g; benzoic acid: 2 g; hydroquinone: 1 g; temperature: 180°C; time: 1 hour

| EXAMPLE | 1 | 2 | 3 | 4 | 5 | 6 | 7 | 8 | 9 | 10 | 11 |
|---|---|---|---|---|---|---|---|---|---|---|---|
| quantity applied [g] | | | | | | | | | | | |
| H₂O | 5 | 30 | 55 | 105 | 5 | 30 | 55 | 5 | 55 | 5 | 55 |
| AN | 424 | 424 | 424 | 424 | 265 | 265 | 265 | 424 | 424 | 265 | 265 |
| IPA | 42 | 42 | 42 | 42 | 21 | 21 | 21 | 21 | 21 | 42 | 42 |
| selectivities [mole.%] | | | | | | | | | | | |
| OHN/AN | 75 | 82 | 86 | 82 | 80 | 93 | 94 | 75 | 82 | 84 | 94 |
| OHN/acetone | 50 | 66 | 74 | 76 | 46 | 68 | 73 | 61 | 78 | 49 | 61 |
| yields [g/g] | | | | | | | | | | | |
| OHN/IPA reacted | 34 | 36 | 100 | 44 | 21 | 35 | 61 | 50 | 107 | 14 | 29 |
| conversion rate [wt.%] | | | | | | | | | | | |
| acetone | 26 | 20 | 16 | 4 | 17 | 10 | 7 | 17 | 7 | 19 | 13 |
| AN | 81 | 81 | 71 | 20 | 79 | 50 | 42 | 73 | 35 | 85 | .70 |

What is claimed is:

1. In a process for preparing 5-oxohexane-nitrile by reaction of acetone with acrylonitrile at from 50°C to 250°C in the presence of from 0.001 to 0.02 mols of an acid per mol of acrylonitrile and from 0.01 to 0.2 mols of a compound per mol of acrylonitrile, said compound being selected from the group consisting of primary amines and Schiff bases, the improvement comprising carrying out the reaction in the presence of water maintained at the rate of from 0.2 to 5 weight percent, calculated on the reaction mixture.

2. A process according to claim 1 wherein the reaction ratio of acetone to acrylonitrile is at a molar proportion of about 1:1 to about 20:1.

3. A process according to claim 2, wherein said compound is selected from the group consisting of alkane primary amines having 1 to 5 carbon atoms, said amines further having a hydroxyl group, said amines further having a carboxylic group, and monocyclic primary means having 6 carbon atoms in the ring structure and 6 to 7 carbon atoms in the total structure, and said Schiff bases which are the condensation product of acetone and a foregoing primary amine.

4. A process according to claim 2 wherein said acid is chosen from the group consisting of formic, acetic, butyric, benzoic, adipic, hydrochloric and phosphoric acids.

5. A process according to claim 4, wherein said reaction is at a pressure of 1 to 50 atmospheres.

* * * * *